United States Patent
Rwei

(10) Patent No.: US 10,994,044 B2
(45) Date of Patent: May 4, 2021

(54) SHAPE MEMORY SPACER FABRIC COMPOSITE

(71) Applicant: National Taipei University of Technology, Taipei (TW)

(72) Inventor: Syang-Peng Rwei, Taipei (TW)

(73) Assignee: TSM SMART MATERIALS CO., LTD, Taoyuan (TW)

(*) Notice: Subject to any disclaimer, the term of this patent is extended or adjusted under 35 U.S.C. 154(b) by 261 days.

(21) Appl. No.: 16/010,465

(22) Filed: Jun. 17, 2018

(65) Prior Publication Data

US 2018/0369444 A1 Dec. 27, 2018

(30) Foreign Application Priority Data

Jun. 23, 2017 (TW) ................... 106121010

(51) Int. Cl.
*A61L 15/26* (2006.01)
*A61F 13/04* (2006.01)
(Continued)

(52) U.S. Cl.
CPC ............. *A61L 15/26* (2013.01); *A61F 13/04* (2013.01); *A61L 31/06* (2013.01); *A61N 1/36014* (2013.01); *A61N 2/002* (2013.01); *A61N 2/02* (2013.01); *A61N 7/00* (2013.01); *B32B 5/026* (2013.01); *B32B 27/12* (2013.01); *D06M 15/507* (2013.01); *A61F 2013/00489* (2013.01); *A61F 2013/00604* (2013.01);
(Continued)

(58) Field of Classification Search
CPC ....... D10B 2401/046; D10B 2403/021–02431; D10B 2509/024; A61F 13/04–048; A61L 2400/16; B32B 2353/00; B32B 2307/546; B32B 2255/26; B32B 5/022–026; A61N 2/02; A61N 1/0404–0496; A61N 2007/0013
USPC ....................................... 602/1–40
See application file for complete search history.

(56) References Cited

U.S. PATENT DOCUMENTS 4,136,686 A * 1/1979 Arluck .................. A61F 5/0118
602/7
4,550,714 A * 11/1985 Talish ...................... A61N 2/02
600/14
(Continued)

FOREIGN PATENT DOCUMENTS

CN 101589087 11/2009
CN 102212966 10/2011
(Continued)

OTHER PUBLICATIONS

Jan. 21, 2020—OA (the OA document is attached in Chinese).

*Primary Examiner* — Catherine B Kuhlman
(74) *Attorney, Agent, or Firm* — IPR Works LLC

(57) ABSTRACT

The invention provides a shape memory spacer fabric composite, being a spacer fabric coated with a shape memory polymer layer, wherein the spacer fabric comprises a first outer layer, a second outer layer and an intermediate spacing layer connecting the first outer layer and the second outer layer; the shape memory polymer layer is made from at least one block or random copolymer selected from the group consisting of the following: polyesters, polyurethanes, polyamides, polyols; the copolymer has at least one phase transition temperature in a range of 40~80° C.

10 Claims, 7 Drawing Sheets

(a)

(b)

(51) Int. Cl.

| | | |
|---|---|---|
| *A61N 1/36* | (2006.01) | |
| *A61N 2/00* | (2006.01) | |
| *A61N 2/02* | (2006.01) | |
| *A61N 7/00* | (2006.01) | |
| *B32B 5/02* | (2006.01) | |
| *B32B 27/12* | (2006.01) | |
| *D06M 15/507* | (2006.01) | |
| *A61F 13/00* | (2006.01) | |
| *A61L 31/06* | (2006.01) | |

(52) U.S. Cl.
CPC ............. *A61F 2013/00621* (2013.01); *A61L 2400/16* (2013.01); *A61N 2007/0013* (2013.01); *B32B 2255/02* (2013.01); *B32B 2255/26* (2013.01); *B32B 2307/546* (2013.01); *B32B 2307/724* (2013.01); *B32B 2535/00* (2013.01); *D10B 2401/046* (2013.01); *D10B 2401/18* (2013.01); *D10B 2509/00* (2013.01)

(56) References Cited

U.S. PATENT DOCUMENTS

| | | | | |
|---|---|---|---|---|
| 6,406,443 | B1* | 6/2002 | Talish | A61N 7/00 601/2 |
| 6,673,029 | B1* | 1/2004 | Watson | A61F 13/04 602/6 |
| 2002/0016618 | A1* | 2/2002 | Da Silva | A61N 1/32 607/72 |
| 2010/0249682 | A1* | 9/2010 | Rousseau | A61F 13/04 602/7 |
| 2013/0298317 | A1* | 11/2013 | Fonte | A41D 13/015 2/414 |
| 2014/0081296 | A1* | 3/2014 | Palmer | A61F 2/0063 606/151 |
| 2015/0045876 | A1* | 2/2015 | Clerc | A61L 31/148 623/1.38 |
| 2015/0299359 | A1* | 10/2015 | Shandas | A61F 2/0063 606/151 |

FOREIGN PATENT DOCUMENTS

| | | | |
|---|---|---|---|
| CN | 102212966 | A * | 10/2011 |
| CN | 102212966 | A | 10/2011 |
| CN | 102757553 | A | 10/2012 |

* cited by examiner

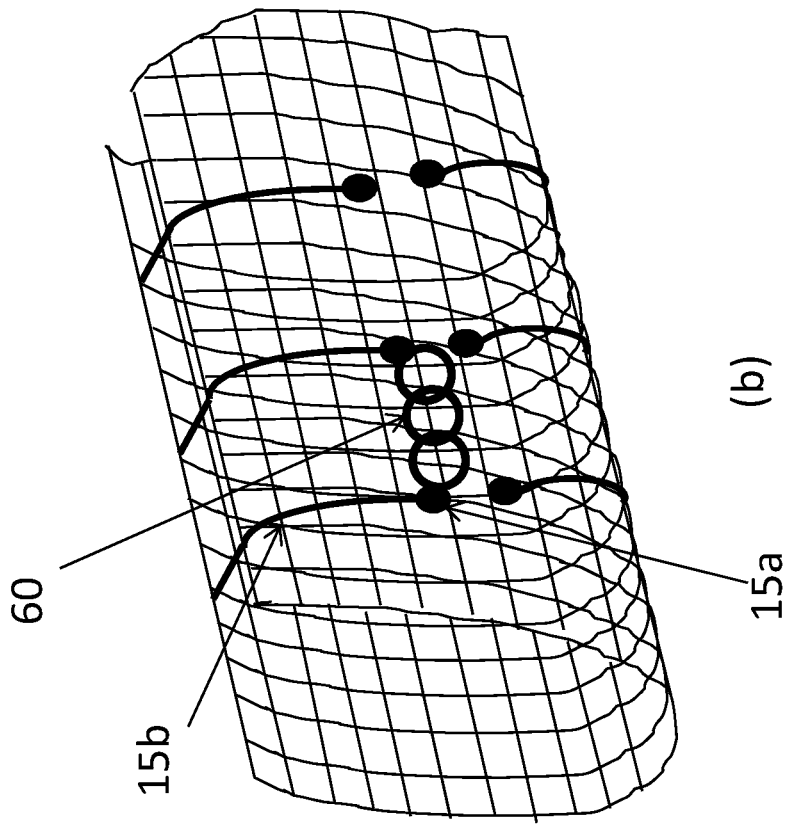
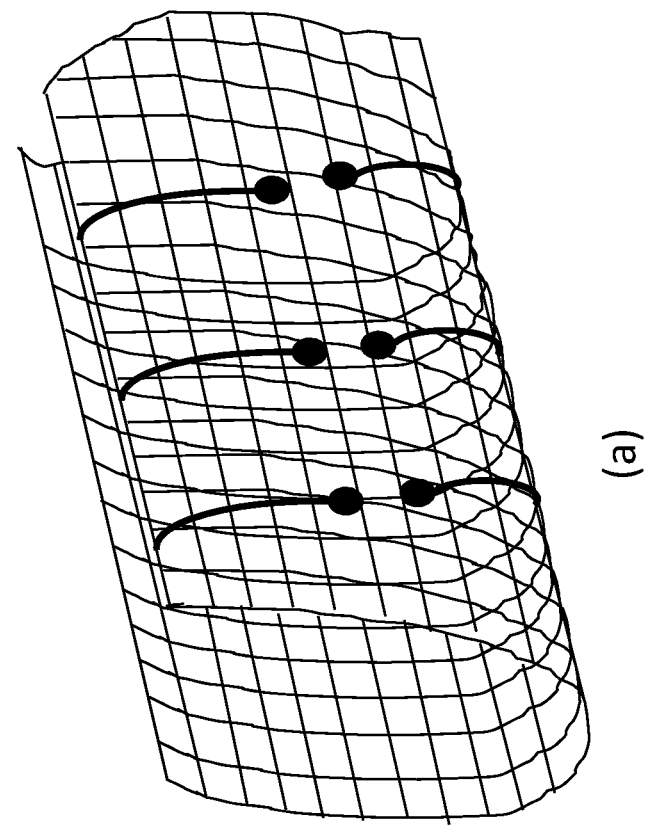
FIG. 4

SHAPE MEMORY SPACER FABRIC COMPOSITE

BACKGROUND OF THE INVENTION a. Field of the Invention

The invention relates to a shape memory spacer fabric composite, particular to a shape memory spacer fabric composite for a fixation device or a support device.

b. Description of the Related Art

Three-dimensional (3-D) fabrics or spacer fabrics have characteristics of being structurally strong, elastic, porous, and light-weight. Applications at all levels are being continuously developed in innovative applications such as apparels, shoe materials, transportation, construction, agriculture, and medical care. The addition of special functions transforms the 3-D fabric to become a smart fabric having intelligent characteristics, for example, the combination of the thermoplastic material with the 3-D fabric described in WO2006/079602 as the fracture fixation device, the orthopedic casting technology described in U.S. Pat. No. 6,482,167, and the like. Because the 3-D fabric has the characteristics of excellent air permeability and light weight, accompanying with the mechanical strength and plasticity of the thermoplastic material, it is very suitable to replace the traditional plaster as a fixation splint or support plate for bone fractures.

A shape-memory macromolecular (polymer) material, being a type of smart material, responses to an external stimulus such as heat, light, electric field, and magnetic field by recovery from a deformed transient state (temporary shape) to its permanent state (initial shape). Such a responsive characteristic has been widely used in, for example, electronic circuit elements, thermal sensors, biomedical fields, etc. Specifically, for example, the previous disclosed shape memory actuators and catheters are described in U.S. Pat. No. 6,740,094, the separation membrane is described in U.S. Pat. No. 5,910,357, the shape memory bra is described in U.S. Patent Publication No. 2016/0044971, and the shoe last system is described in the Taiwan patent TWI556757.

The principle of shape plasticity and shape memory is as follows. Usually, a material having two glass transition temperatures ($T_g$) and 1~2 melting temperatures ($T_m$) to thereby derive 2 to 3 plateau regions is used. The deformation in the high-temperature plateau region causes the temperature to drop to a low temperature plateau suddenly and the molecules are frozen without being relaxed. At this time, the deformed shape needs to wait until the temperature returns to the high-temperature plateau again to have the recovery driving force. However, although shaping a thermoplastic material can be achieved, whether or not it returns from the deformed shape to the original shape depends on the level of relaxation of the molecule after deformation. If it undergoes longer relaxation at high temperatures after deformation, the level of "memory recovery" to the original shape with no external force will not be significant. If there are 3 plateau regions, by inserting an intermediate temperature plateau region (memory recovery region) between the high-temperature plateau region and the low-temperature plateau region, the relaxation time after thermoplastics becomes unimportant, and as long as the temperature is within the memory recovery zones, the material can be shaped and then cooled to the low-temperature plateau region where it can be utilized. If deformation occurs while being in use, the material can be recovered to the original shape as long as it is heated up to the memory recovery region.

As the shape memory polymer material is applied to 3-D fabrics, compared to the case of using a thermoplastic material, in addition to the thermoplastic shape, because of the shape memory property and having two to three memory shapes, the 3-D fabrics can have more diversified functions.

Traditionally, plasters have been used to fix the fracture sites (usually being limbs) or a dressing band made of thermoplastic polyolefin as described in U.S. Pat. No. 7,867,180 has been used as a fixation or support device for the fracture sites. However, the plaster or dressing band is inconvenient in use and has the problem of insufficient ventilation. Furthermore, during the fracture site is fixed with plasters or dressing strips, the plasters or dressing strips are not easily temporarily dismantled and it is also not possible to use any external device to provide a mechanism to assist the recovery of the fracture site. The plasters or dressing strips are simply for fixation and/or support and do not have the function to promote the growth of bone cells. According to the study of promoting the growth of bone cells, all the effective methods need to provide regular (for example, daily) stimulation such as electric field, magnetic field, ultrasonic wave, shock wave, etc. However, it is not easy to perform such treatment after applying a fixation or support device to a fracture site in practice.

BRIEF SUMMARY OF THE INVENTION

In light of the above background, in order to fulfill the requirements of the industry, one object of the invention provides a shape memory spacer fabric composite. By combining the shape memory polymer and the 3-D fabric, the shape memory effect of the 3-D fabric can be achieved. By adjusting the glass transition temperature ($T_g$) and the melting point ($T_m$), molecular crosslinking degree or crystallinity of the shape memory polymer, the specific mechanical strengths can be obtained. The shape-memory three-dimensional textile composite materials having the different molecular relaxation time (i.e. thermoplastic operating time) can have advantages of excellent ability to follow the shape of the object to be fixed and excellent operability, in addition to light weight and excellent air permeability.

Another object of the invention provides a fixation device. The fixation device uses a shape-memory three-dimensional fabric composite material and is to replace the conventional plaster to fix or support a specific body part to have advantages of light weight, excellent air permeability, excellent ability to follow the shape of the applied object, and excellent operability. In addition, the fixation or support device can provide stimulation such as electric field, magnetic field, ultrasonic wave, shock wave, etc. to fractured bones to promote the growth of bone cells and assist the recovery of the fractured bones of the user.

Other objects and advantages of the invention can be better understood from the technical characteristics disclosed by the invention. In order to achieve one of the above purposes, all the purposes, or other purposes, one embodiment of the invention provides a shape memory spacer fabric composite. The shape memory spacer fabric composite is a spacer fabric (3-D fabric) coated with a shape memory polymer layer, wherein the spacer fabric comprises a first outer layer, a second outer layer and an intermediate spacing layer connecting the first outer layer and the second outer layer; the shape memory polymer layer is made from at least one block or random copolymer selected from the group consisting of the following: polyesters, polyurethanes, polyamides, polyols; the copolymer has at least one phase transition temperature in a range of 40~80° C.

Furthermore, one other embodiment of the invention provides a fixation device using the shape memory spacer fabric composite according to the present invention to fix a specific body part of a user.

One other embodiment of the invention provides a support device using the shape memory spacer fabric composite according to the present invention to support a specific body part of a user.

In one embodiment, the copolymer has Young's modulus more than $10^8$ Pa at the temperature below the smallest phase transition temperature among the at least one phase transition temperature and the shape memory spacer fabric composite has a flexural strength more than 50 kgf/cm$^2$ according ASTM D790.

In one embodiment, the block or random copolymer has two phase transition temperatures, a first phase transition temperature which is within 0~37° C. and a second phase transition temperature which is within 46~80° C.; the copolymer has Young's modulus being more than $10^6$ Pa at the temperature below the second phase transition temperature, has Young's modulus being within $10^6$ Pa~$10^8$ Pa at the temperature between the second phase transition temperature and the first second phase transition temperature, and has Young's modulus being more than $10^8$ Pa at the temperature below the first phase transition temperature.

In one preferred embodiment, the block or random copolymer is polyester(s) or polyurethane(s).

In one preferred embodiment, the shape memory polymer layer is a polyester random copolymer and the polyester is formed by polymerization of ethylene glycol, sebacic acid, hexamethylene diamine and benzenetricarboxylic acid.

In one preferred embodiment, the shape memory polymer layer is a polyurethane random copolymer and the polyurethane is formed by mixing or blending polyurethanes or mixing or blending polyurethanes with some other inorganic compounds and the polyurethanes are mutually dissolvable or slightly mutually dissolvable.

In one preferred embodiment, the surface of the shape memory polymer layer on one of the two outer layers or both has at least one circuitry pattern layer thereon; the circuitry pattern layer comprises at least one conducting circuit formed by conductive materials and a plurality of contact points for connecting an electronic component.

In one preferred embodiment, the circuitry pattern layer further comprises a plurality of conductive terminals at the edge of the outer layer and electromagnetic pulse waves are provided to a user through the conductive terminals and the contact points. In one preferred embodiment, electric pulses are provided to a user through conductive terminals and the contact points when the contact points are connected to electrode pads.

In one preferred embodiment, ultrasonic waves are provided to a user through the conductive terminals and the contact points when the contact points are connected to an ultrasonic induction element. The ultrasonic induction element can be an ultrasound probe.

According to the shape memory spacer fabric composite of the present invention, the shape-memory composite materials having the different molecular relaxation time (i.e. thermoplastic operating time) and the specific mechanical strengths for orthopedic fixation or support can be achieved and the advantages of light weight, excellent air permeability, excellent ability to follow the shape of the object to be fixed, and excellent operability can be obtained. The characteristics of the composite are suitable to be applied in various application fields such as apparels, shoe materials, and transportation, construction, agriculture, and medical care. Furthermore, according to the fixation device and the support device of the present invention, the advantages of light weight, excellent air permeability, excellent ability to follow the shape of the object to be fixed, and excellent operability can be obtained. In addition, the fixation or support device can provide stimulation such as electric field, magnetic field, ultrasonic wave, shock wave, etc. to fracture bones to promote the growth of bone cells and assist the recovery of the fractured bones of the user. One example of the use of the support device of the present invention is a device to support a spine or a device to treat scoliosis.

Other objectives, features and advantages of the invention will be further understood from the further technological features disclosed by the embodiments of the invention wherein there are shown and described preferred embodiments of this invention, simply by way of illustration of modes best suitable to carry out the invention.

BRIEF DESCRIPTION OF THE DRAWINGS

FIG. 4 shows a schematic diagram illustrating a shape memory spacer fabric composite according to another embodiment of the invention.

DETAILED DESCRIPTION OF THE INVENTION

Figure 1:
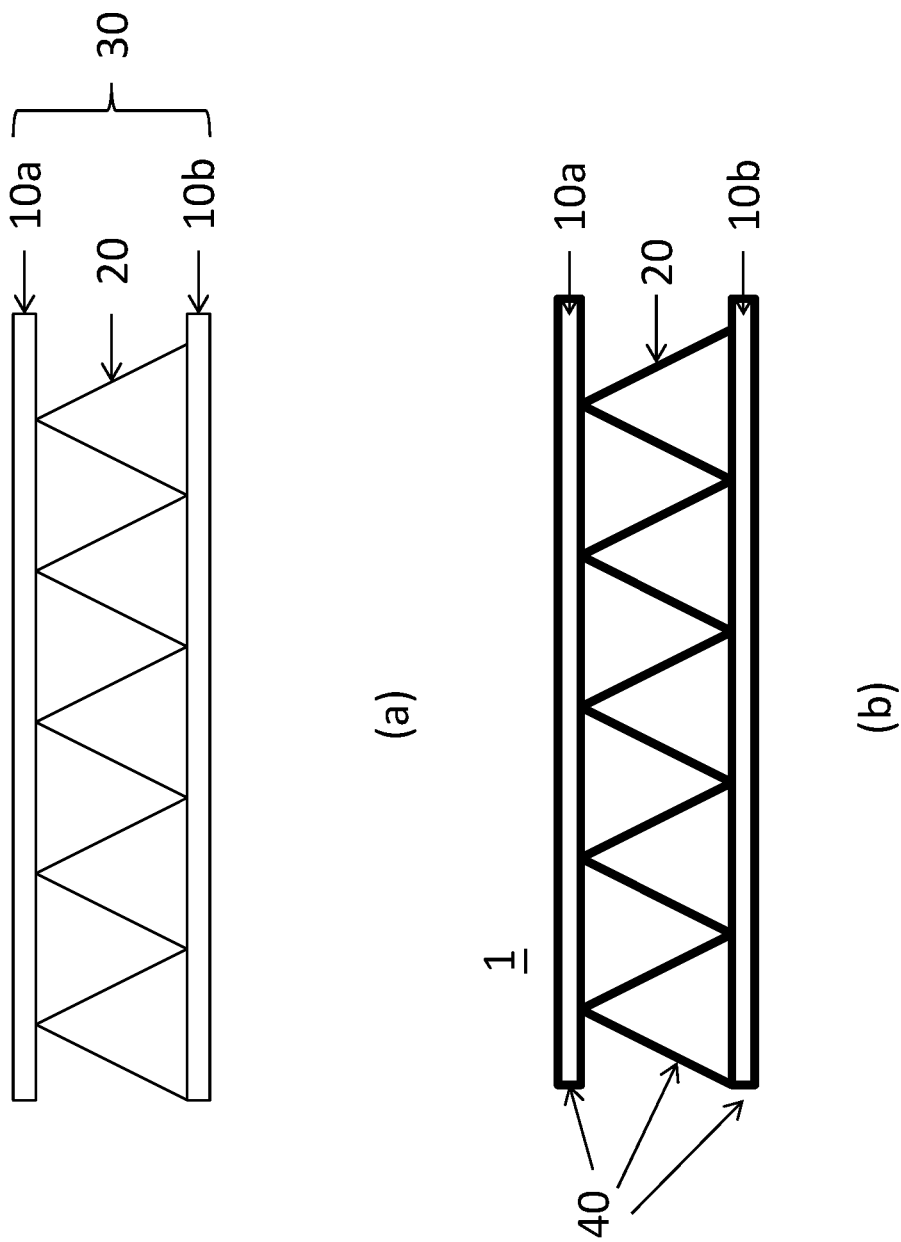
FIG. 1 shows a cross-sectional schematic diagram illustrating a shape memory spacer fabric composite according to one embodiment of the invention.

In the following detailed description of the preferred embodiments, reference is made to the accompanying drawings which form a part hereof, and in which are shown by way of illustration specific embodiments in which the invention may be practiced. The drawings are only schematic and the sizes of components may be exaggerated for clarity. It is to be understood that other embodiments may be utilized and structural changes may be made without departing from the scope of the invention. Also, it is to be understood that the phraseology and terminology used herein are for the purpose of description and should not be regarded as limiting. The common structures and elements that are known to everyone are not described in details to avoid unnecessary limits of the invention. In the following examples, the description of the direction, such as upper, lower, left, right, front or rear, etc., is referred to the direction of the drawing. Besides, the meaning of "A layer (or element) is on B layer (element)" includes, but not limited to, "A layer is directly laminated and contact with B layer". For example, a layer (C layer) may be existed between A layer and B layer. Some preferred embodiments of the present invention will now be described in greater detail in the following.

Figure 2:
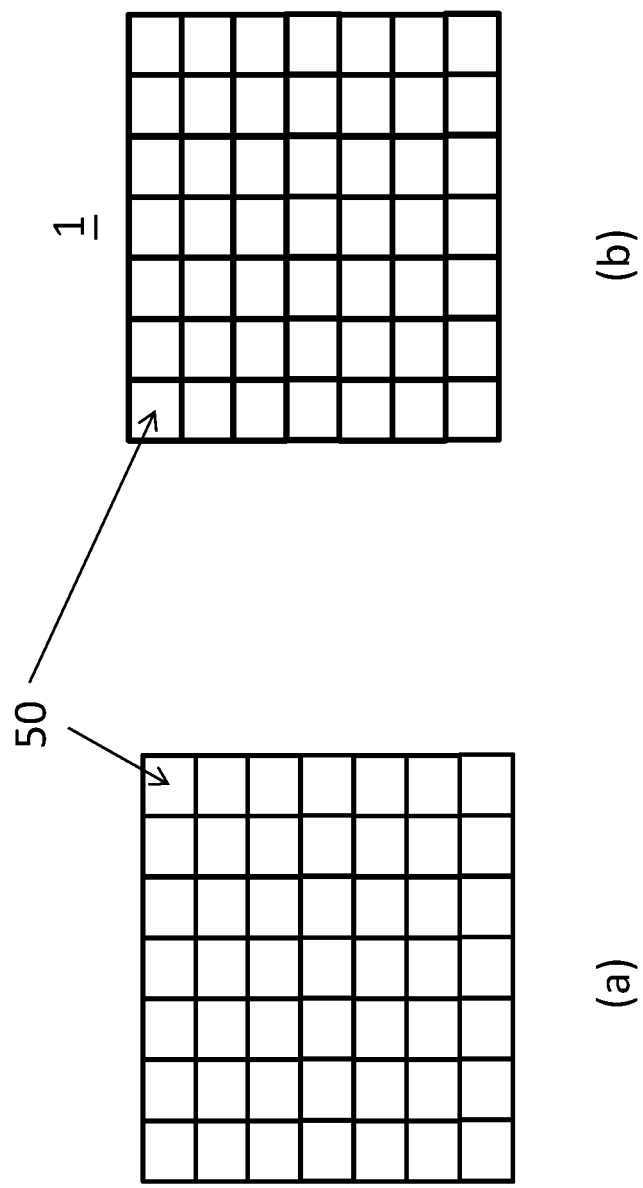
FIG. 2 shows a top-view schematic diagram illustrating a shape memory spacer fabric composite shown in FIG. 1.

FIG. 1 shows a cross-sectional schematic diagram illustrating a shape memory spacer fabric composite according to one embodiment of the invention where (a) shows a spacer fabric 30 comprises two outer layers 10a and 10b, and an intermediate spacing layer 20 connecting the outer layer 10a and the outer layer 10b; and (b) shows a shape memory spacer fabric composite 1 has a shape memory polymer layer 40 which covers the surfaces of the two outer layers 10a and 10b, and the intermediate spacing layer 20. FIG. 2 shows a top-view schematic diagram illustrating a shape memory spacer fabric composite shown in FIG. 1.

The spacer fabric 30 is consisted of two outer layers 10a and 10b, and an intermediate spacing layer 20 connecting the outer layer 10a and the outer layer 10b. The two outer layers 10a and 10b have meshes, such as rhomboid shaped meshes and the intermediate spacing layer is mono yarn. The structure of the spacer fabric is like a sandwich and thus also called "sandwich 3-D fabric". The high precision warp knitting machine can be used to make the spacer fabric using mainly polymeric synthetic fibers. The two outer layers 10a and 10b were supported by dense networks from the intermediate spacing layer 20 and the surface meshes do not have large deformation to strengthen the mechanical property and enhance the color fastness. The special structure of the spacer fabric has the following advantages: (1) better air permeability and better support compared to the usual flat fabric; (2) good shock resistance, elastic recovery, and extendibility; (3) good fastness, abrasion resistance and fastness to wash; and (4) multi-functionality and versatility by combining with other composite materials. The spacer fabric (3-D fabric) can be extensively applied in the fields, such as cloths, shoe materials, mattresses, cap materials, air permeable pads, sports protective materials, medical composite materials. The spacer fabric 30 is commercially available.

The shape memory polymer layer 40 can be formed by coating, dipping or impregnating the spacer fabric 30 in a solution including a shape memory polymer composition to form a coating film on the surfaces of the spacer fabric 30 and then drying the coating film to become the shape memory polymer layer 40. The shape memory polymer composition may comprise a shape memory polymer and solvent. By adjusting the viscosity and the solid content, the shape memory polymer composition can be coated or impregnated to laminate on the surfaces of the spacer fabric 30 to achieve the ratio of the dried weight ($W_p$) of the shape memory polymer layer 40 to the original weight ($W_{3D}$) of the spacer fabric 30=1~5, that is $W_p/W_{3D}$=1~5, preferably $W_p/W_{3D}$=3~5. One the other hand, the shape memory polymer layer is made from at least one block or random copolymer selected from the group consisting of the following: polyesters, polyurethanes, polyamides, polyols. The copolymer has a phase transition temperature in a range of 40~80° C. It should be noted that, as shown in FIG. 2, the spacer fabric 30 still has the meshes 50 after the shape memory polymer layer 40 is formed on the surfaces of the spacer fabric 30, that is the shape memory spacer fabric composite 1 according to the present invention has the three-dimensional mesh structure. The dimension of the mesh 50 (hollow hole) of the composite is smaller than that of the original uncoated spacer fabric. The hole shrinkage ratio ((Db~Df)/Db) of the mesh 50 is preferably less than 80%, more preferably less than 50%, and further more preferably less than 40%, where Db is the average diameter of the mesh 50 before formation of the shape memory polymer layer 40 and Df is the average diameter of the mesh 50 after formation of the shape memory polymer layer 40. The lower the hole shrinkage ratio the higher the air permeability of the shape memory spacer fabric composite 1. Specifically, the shape memory spacer fabric composite according to the present invention has the air permeability more than 100 cfm (ft$^3$/min) based on ASTM D737, preferably more than 300 cfm and more preferably more than 500 cfm.

In one embodiment, the copolymer has Young's modulus more than $10^8$ Pa. The copolymer has Young's modulus more than $10^8$ Pa at the temperature below the smallest phase transition temperature among the at least one phase transition temperature. Furthermore, according to ASTM D790 (Standard Test Methods for Flexural Properties of Unreinforced and Reinforced Plastics and Electrical Insulating Materials), a specimen with a width of 14 mm and a thickness of 7.5 mm is used in the three-point bending test, the testing speed is set to 3.2 mm/min, the radii of the support and the loading are 9 mm, the distance of the supports is 85 mm, and the value at the 5% deformation without breaking is the flexural strength. The shape memory spacer fabric composite has a flexural strength more than 50 kgf/cm$^2$. The material of the shape memory polymer layer 40 is preferably polyesters or polyurethanes. For example, the polyester is formed by polymerization of ethylene glycol, sebacic acid, hexamethylene diamine and benzenetricarboxylic acid. In another example, the polyester can be synthesized by the methods disclosed in Taiwan patent No. 1443124 and 1297699. In another embodiment, the shape memory polymer layer is formed by a polyurethane random copolymer and the polyurethane is formed by mixing or blending polyurethanes or mixing or blending polyurethanes with some other inorganic compounds and the polyurethanes are mutually dissolvable or slightly mutually dissolvable. Besides, the shape memory polymer layer can be made from a mixture of at least one block or random copolymer and at least one inorganic filler. The examples of the inorganic filler include, but not limited to, talc, clay, SiO$_2$ nano powders. The weight percentage of the inorganic filler in the shape memory polymer layer depends on the required toughness and hardness of the composite. For examples, the shape memory polymer layer can be made from a mixture of polyurethane and the inorganic filler, such as SiO$_2$ nano powders. The addition quantity of the filler can be 1~50 wt %, preferably 5~20 wt %, more preferably 8~15 wt %.

In another embodiment, the block or random copolymer has a first phase transition temperature which is within 0~37° C. and a second phase transition temperature which is within 46~80° C.; the copolymer has Young's modulus being more than $10^6$ Pa at the temperature below the second phase transition temperature, has Young's modulus being within $10^6$ Pa~$10^8$ Pa at the temperature between the second phase transition temperature and the first second phase transition temperature, and has Young's modulus being more than $10^8$ Pa at the temperature below the first phase transition temperature. That is, the shape memory spacer fabric composite is hard at the room temperature and is softened at the temperature between the second phase transition temperature and the first second phase transition temperature. The shaping duration of the shape memory spacer fabric composite is about 60~300 seconds, and preferably about 100~150 seconds.

Figure 3:
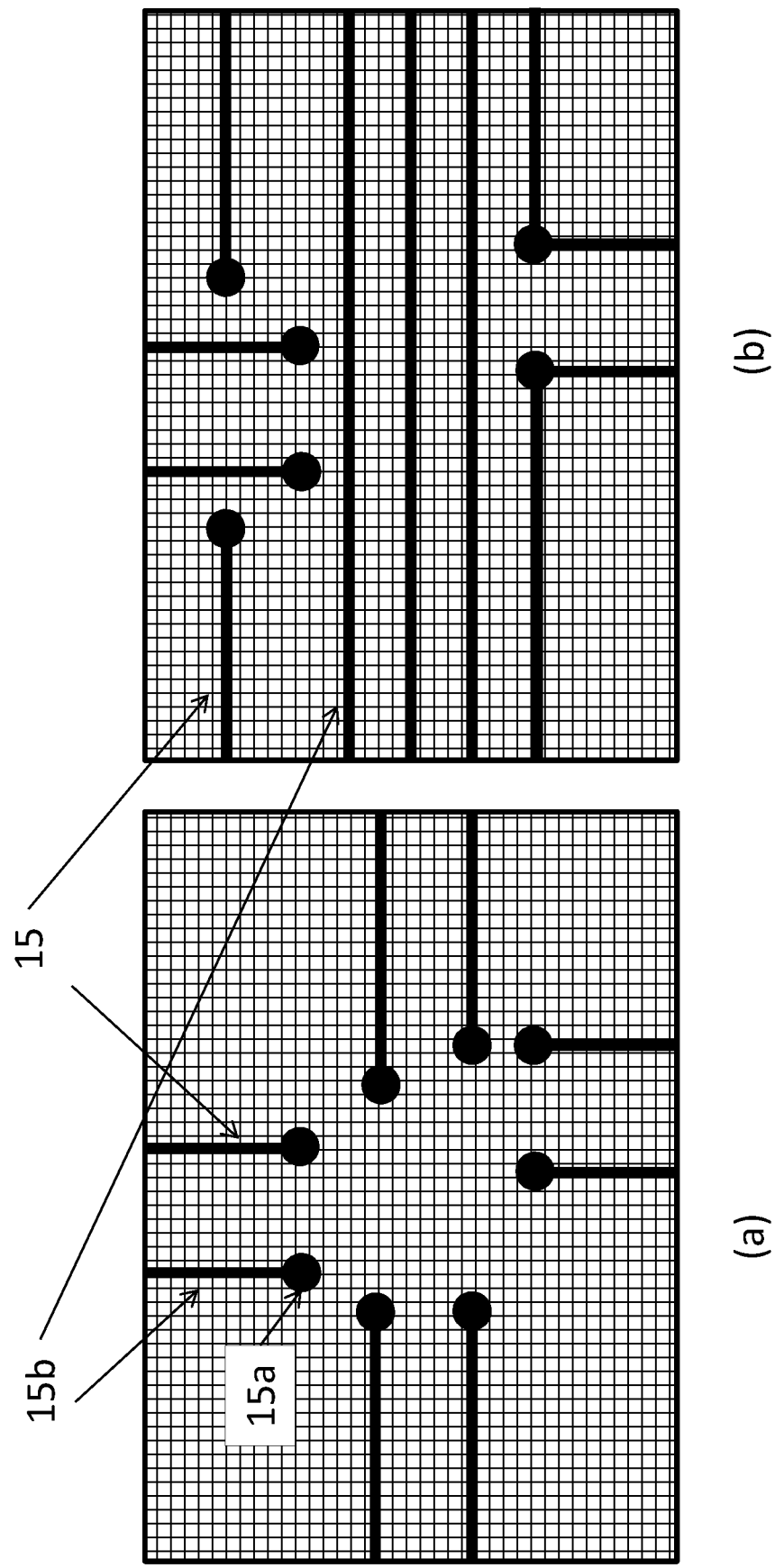
FIG. 3 shows a schematic diagram illustrating the circuitry pattern layer of the shape memory spacer fabric composite according to one embodiment of the invention.

FIG. 3 shows a schematic diagram illustrating the circuitry pattern layer 15 of the shape memory spacer fabric composite 1 according to one embodiment of the invention.

The surface of the shape memory polymer layer 40 on one of the two outer layers 10a and 10b or both has at least one circuitry pattern layer 15 thereon. The circuitry pattern layer 15 comprises at least one conducting circuit formed by conductive materials and a plurality of contact points for connecting an electronic component where 15a represents the contact points and 15b represents the conductive lines. FIGS. 3(a) and (b) show two different types of circuitry pattern layers including a plurality of contact points 15a and conductive lines 15b or including only conductive lines 15b. FIG. 4 shows a schematic diagram illustrating a shape memory spacer fabric composite according to another embodiment of the invention where (a) shows the composite is bended to a cylinder-like shape and has the circuitry pattern layer 15 facing outside; and (b) shows the electronic element 60 is connected to the two contact points 15a. For example, the electronic element 60 is electromagnetic coils connected to the contact points 15a and can provide electromagnetic pulses (applying pulsed electromagnetic field therapy) to a specific position through the conductive lines 15b after the circuit is connected with an external electromagnetic pulse source. In another example, the circuitry pattern layer can face inside. The words "outside" and "inside" mean the outside and the inside of the hollow cylinder when the composite is bended to a cylinder-like shape. That is, the circuitry pattern layer 15 can be provided on the surface of the shape memory polymer layer 40 of one of the two outer layers (10a or 10b) or both (10a and 10b). The forming method can be for example the ink-jet coating, printing or thermal transfer method, and preferably the thermal transfer method. The installation of the coil(s) 60 shown in FIG. 4 is only one example and the number of coils and the positions can be adjusted according to the actual application. Furthermore, the electrode pad can be used instead of the electromagnetic coil to provide electric pulses or ultrasound waves.

Figure 5:
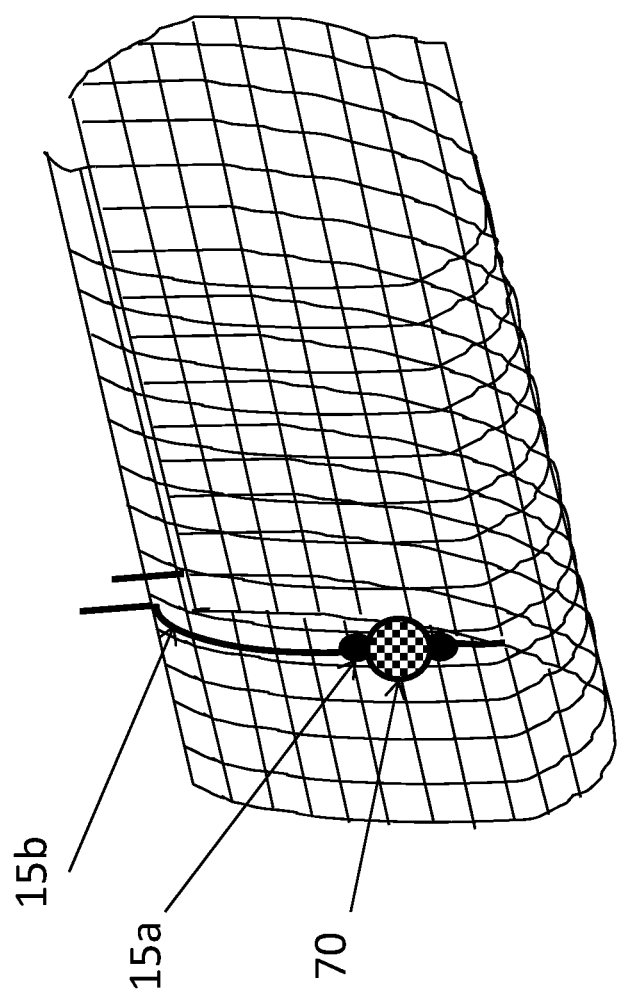
FIG. 5 shows a schematic diagram illustrating a shape memory spacer fabric composite according to another embodiment of the invention.

FIG. 5 shows a schematic diagram illustrating a shape memory spacer fabric composite according to another embodiment of the invention. The ultrasound probe 70 is connected to the contact points 15a and the circuitry pattern layer 15 is positioned at the inside surface of the cylindrical shape of the shape memory spacer fabric composite, i.e. near the side of the bone fracture portion.

Figure 6:
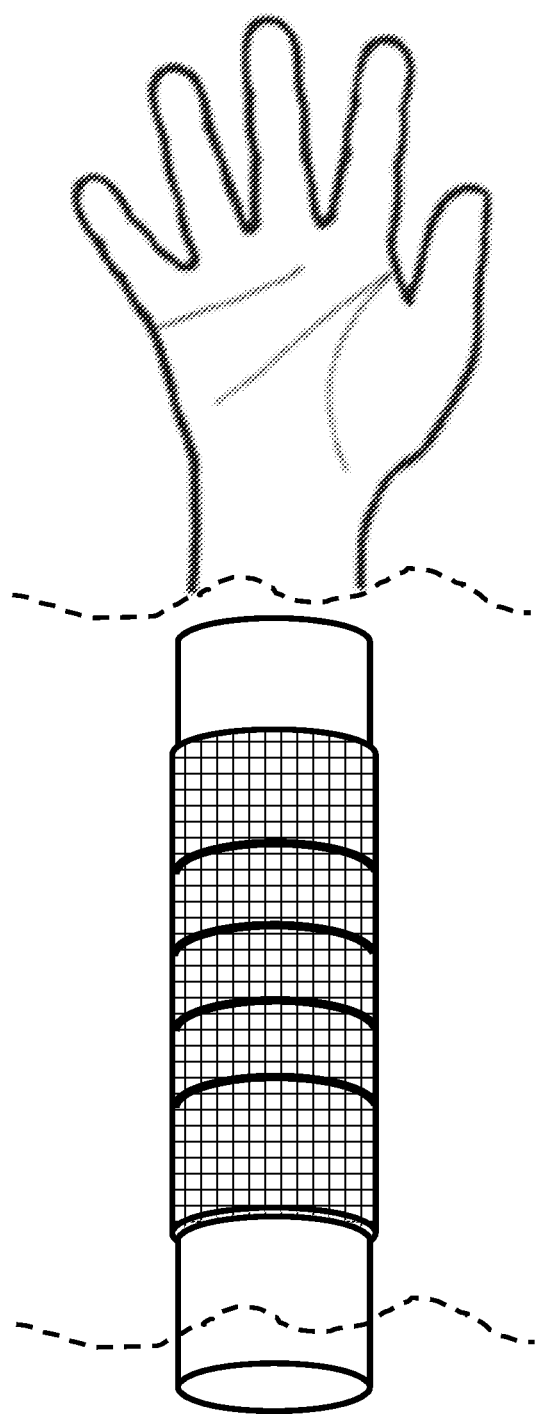
FIG. 6 shows a schematic diagram illustrating a fixation device using the shape memory spacer fabric composite to a facture portion.

FIG. 6 shows a schematic diagram illustrating a fixation device using the shape memory spacer fabric composite to a facture portion. Although the facture portion is a portion of an arm shown in FIG. 6, the shape memory spacer fabric composite can be utilized to, but not limited to, any portion of a human being or a live animal. The shape memory spacer fabric composite according to the present invention can be used to provide electromagnetic pulse waves, ultrasonic waves or electric pulses through an external device and the electromagnetic pulse waves, ultrasonic waves or electric pulses are introduced through the circuitry pattern layer 15 to a specific portion of the user to assist bone cell growth.

Figure 7:
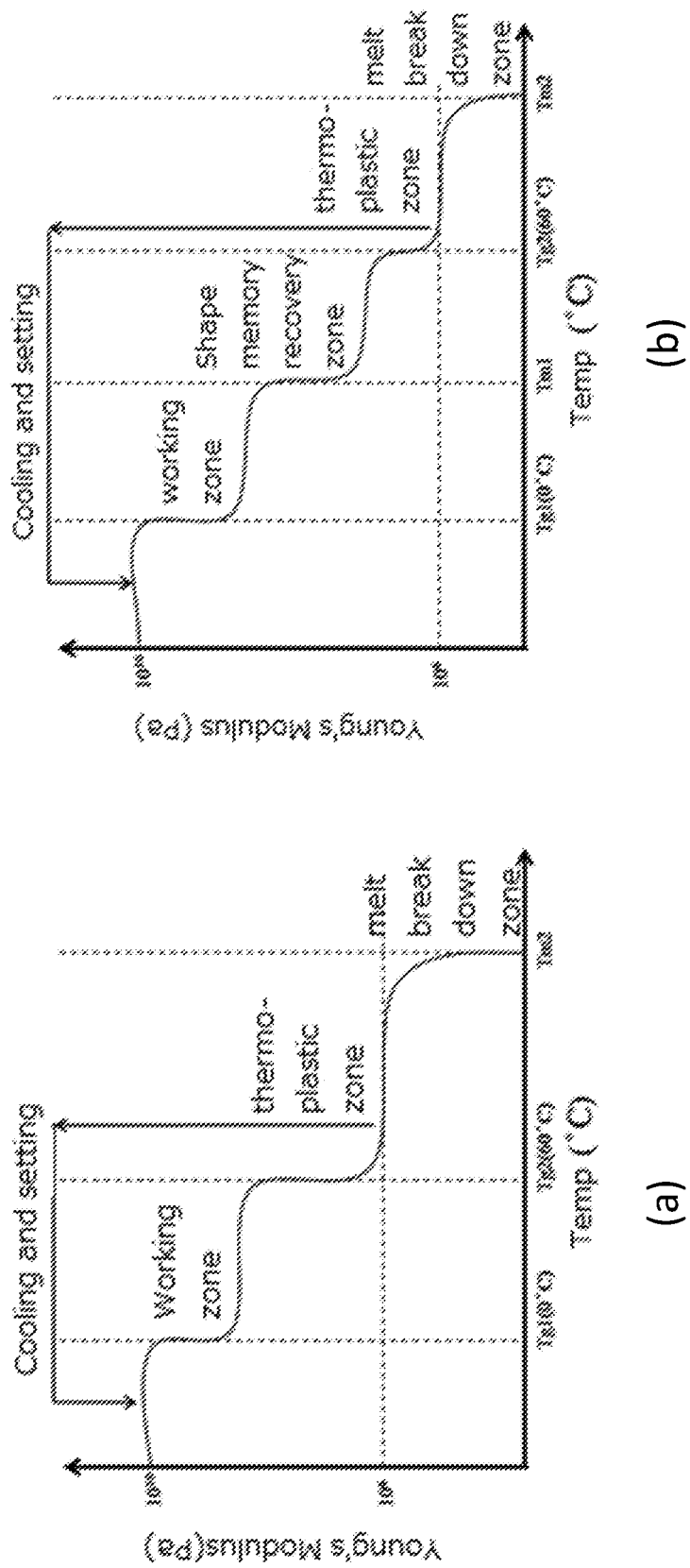
FIG. 7 shows a plot of Young's modulus versus temperature when the shape memory spacer fabric composite is used in a fixation device according to one embodiment of the invention.

FIG. 7 shows a plot of Young's modulus versus temperature when the shape memory spacer fabric composite is used in a fixation device according to one embodiment of the invention where (a) and (b) show the characteristic of the two different memory spacer fabric composites. As shown in FIG. 7(a), the composite has two $T_g$ and one $T_m$ while the composite has two $T_g$ and two $T_m$ in FIG. 7(b).

Furthermore, the fixation device according to the present invention is not limited to human beings or fraction portions. For example, it can be used to fix the fracture portion of an animal. In addition, the present invention provides a support device to be used at any body part or any part of a live animal whenever it is needed. Because the shape memory spacer fabric composite possesses the good mechanical strength, it can be used to support the spine or correct scoliosis. Besides, the electric field, magnetic field, ultrasound, or pules can be provided to stimulate any portion through the fixation device or the support device according to the present invention.

In conclusion, according to the shape memory spacer fabric composite of the present invention, the shape-memory composite materials having the different molecular relaxation time (i.e. thermoplastic operating time) and the specific mechanical strengths for orthopedic fixation or support can be achieved and the advantages of light weight, excellent air permeability, excellent ability to follow the shape of the object to be fixed, and excellent operability can be obtained. The characteristics of the composite are suitable to be applied in various application fields such as apparels, shoe materials, and transportation, construction, agriculture, and medical care. Furthermore, according to the fixation device and the support device of the present invention, the advantages of light weight, excellent air permeability, excellent ability to follow the shape of the object to be fixed, and excellent operability can be obtained. In addition, the fixation or support device can provide stimulation such as electric field, magnetic field, ultrasonic wave, shock wave, etc. to fracture bones to promote the growth of bone cells and assist the recovery of the fractured bones of the user.

The foregoing description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the invention as defined by the following claims. Moreover, no element and component in the present disclosure is intended to be dedicated to the public regardless of whether the element or component is explicitly recited in the following claims. Each of the terms "first" and "second" is only a nomenclature used to modify its corresponding element. These terms are not used to set up the upper limit or lower limit of the number of elements.

What is claimed is:

1. A shape memory spacer fabric composite, comprising a spacer fabric coated with a shape memory polymer layer, wherein the spacer fabric comprises a first outer layer, a second outer layer and an intermediate spacing layer connecting the first outer layer and the second outer layer; the shape memory polymer layer is a polyester random copolymer; the polyester random copolymer has at least one phase transition temperature, wherein the polyester comprises ethylene glycol, sebacic acid, hexamethylene diamine and benzenetricarboxylic acid.

2. The composite as claimed in claim 1, wherein the surface of the shape memory polymer layer on one of the two outer layers or both has at least one circuitry pattern layer thereon; the at least one circuitry pattern layer comprises at least one conducting circuit formed by conductive materials and a plurality of contact points for connecting an electronic component.

3. The composite as claimed in claim 2, wherein the at least one circuitry pattern layer further comprises a plurality of conductive terminals at the edge of the one of the two outer layers or both and the composite is configured to provide electromagnetic pulse waves to a user through the conductive terminals and the contact points.

4. The composite as claimed in claim 2, wherein the at least one circuitry pattern layer further comprises a plurality of conductive terminals at the edge of the one of the two outer layers or both and the composite is configured to provide ultrasonic waves to a user through the conductive terminals and the contact points when the contact points are connected to an ultrasonic induction element.

5. The composite as claimed in claim 4, wherein the ultrasonic induction element is an ultrasound probe.

6. The composite as claimed in claim 2, wherein the at least one circuitry pattern layer further comprises a plurality of conductive terminals at the edge of the one of the two outer layers or both and the composite is configured to provide electric pulses to a user through the conductive terminals and the contact points when the contact points are connected to electrode pads.

7. The composite as claimed in claim 1, wherein the shape memory polymer layer is made from a mixture of the polyester random copolymer and at least one inorganic filler.

8. A fixation device, configured to fix a specific portion of a user by using a shape memory spacer fabric composite, wherein the shape memory spacer fabric composite is a spacer fabric coated with a shape memory polymer layer, wherein the spacer fabric comprises a first outer layer, a second outer layer and an intermediate spacing layer connecting the first outer layer and the second outer layer; the shape memory polymer layer is a polyester random copolymer; the polyester random copolymer has at least one phase transition temperature, wherein the polyester comprises ethylene glycol, sebacic acid, hexamethylene diamine and benzenetricarboxylic acid.

9. The fixation device as claimed in claim 8, wherein the shape memory spacer fabric composite is configured to provide electromagnetic pulse waves, ultrasonic waves or electric pulses through an external device to a specific portion of the user to assist bone cell growth.

10. A support device, configured_to support a specific portion of a user by using a shape memory spacer fabric composite; wherein the shape memory spacer fabric composite is a spacer fabric coated with a shape memory polymer layer, wherein the spacer fabric comprises a first outer layer, a second outer layer and an intermediate spacing layer connecting the first outer layer and the second outer layer; the shape memory polymer layer is a polyester random copolymer; the polyester random copolymer has at least one phase transition temperature wherein the polyester comprises ethylene glycol, sebacic acid, hexamethylene diamine and benzenetricarboxylic acid.

* * * * *